(12) United States Patent
Buijink

(10) Patent No.: US 8,664,412 B2
(45) Date of Patent: Mar. 4, 2014

(54) EPOXIDATION PROCESS

(75) Inventor: Jan-Karel Frederik Buijink, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 13/811,283

(22) PCT Filed: Jul. 14, 2011

(86) PCT No.: PCT/EP2011/062040
§ 371 (c)(1),
(2), (4) Date: Jan. 21, 2013

(87) PCT Pub. No.: WO2012/010491
PCT Pub. Date: Jan. 26, 2012

(65) Prior Publication Data
US 2013/0116454 A1 May 9, 2013

(30) Foreign Application Priority Data
Jul. 19, 2010 (EP) ..................... 10170027

(51) Int. Cl.
*C07D 301/02* (2006.01)
(52) U.S. Cl.
USPC ....................................... 549/518
(58) Field of Classification Search
USPC ....................................... 549/518
See application file for complete search history.

(56) References Cited

U.S. PATENT DOCUMENTS

| | | | | |
|---|---|---|---|---|
| 3,351,635 A * | 11/1967 | Kollar | ............................ | 549/529 |
| 3,829,392 A | 8/1974 | Wulff | ............................ | 252/430 |
| 3,923,843 A | 12/1975 | Wulff | ............................ | 260/348.5 |
| 6,011,162 A | 1/2000 | Han et al. | ...................... | 549/529 |
| 6,114,552 A | 9/2000 | Han et al. | | |
| 6,592,764 B1 | 7/2003 | Stucky et al. | | |
| 2008/0289248 A1 | 11/2008 | Gao | ................ | 44/308 |
| 2009/0216033 A1 | 8/2009 | Lekhac | ......................... | 549/523 |
| 2009/0253941 A1 | 10/2009 | Deshmukh et al. | ........... | 568/448 |

FOREIGN PATENT DOCUMENTS

| | | | | |
|---|---|---|---|---|
| CN | 1346791 | 8/2001 | .............. | C01B 39/00 |
| CN | 1390784 | 1/2003 | | |
| CN | 101091921 | 12/2007 | .............. | B01J 28/89 |
| EP | 0345856 | 12/1989 | .............. | B01J 21/06 |
| EP | 734764 | 10/1996 | .............. | B01J 21/06 |
| EP | 1567261 | 6/2004 | | |
| WO | WO0248126 | 6/2002 | .......... | C07D 301/00 |
| WO | WO2004050233 | 6/2004 | | |
| WO | WO2004092052 | 10/2004 | .............. | B82B 3/00 |
| WO | WO2005008813 | 1/2005 | | |
| WO | WO2007069867 | 6/2007 | | |

OTHER PUBLICATIONS

Zhao et. al.; "Designed synthesis of mesoporous solids via nonionic-surfactant-templating approach"; Chem.Comm.; pp. 897-926; 2007.

Zhu, Jin-hua, et al., "Synthesis of Ti-SBA-15 Molecular Sieve by Hydrothermal Method and Study of Catalytic Performance Thereof", Fundan University-Shanghai, Acta Chimica Sinica, vol. 61, 2003, No. 2, pp. 202-207.

Chiker, F., et al., "New Ti-SBA Mesoporous Solids Functionnalized Under Gas Phase Conditions: Characterisation and Application to Selective Oxidation of Alkenes", France, Applied Catalysis A: General 243 (2003) pp. 309-321.

Chicker, F., et al., Optimisation of Gas Phase Deposition of Titanium on Mesoporous Silica SBA-15: Active Site Counting and Catalytic Activity in Cyclohexene Expoxidation, France, Applied Catalysis A: General 259 (2004) pp. 153-162.

Chen, Y. et al., "Direct Synthesis, Characterization and Catalytic Activity of Titanium-Substituted SBA-15 Mesoporous Molecular Sieves", Applied Catalysis A: General vol. 273 (2004), Issues 1-2, pp. 185-191.

Luan Zhaohua et al., "Incorporation of Titanium Into Mesoporous Silica Molecular Sieve SBA-15", University of Houston, Chemical Material 1999, vol. 11, pp. 3680-3886.

Newalkar, Bharat L. et al., "Direct Synthesis of Titanium-Substituted Mesoporous SBA-15 Molecular Sieve Under Microwave-Hydrothermal Conditions", Pennsylvania State University, Chemical Material, 2001, vol. 3, pp. 552-557.

Wu, Peng & Tasumi, Takashi, "Postsynthesis, Characterization, and Catalytic Properties in Alkene Expoxidation of Hydrothermally Stable Mesoporous Ti-SBA-15", Tokyo Institute of Engineering. Chemical Material 2002, vol. 4, pp. 1657-1664.

Chu, H. et al., Synthesis of Ti-Containiog Mesoporous Silicates From Inorganic Titanium Sources, Catalysis Today, (2009) doi:10.1016/j.cafford.2009.03.008, China.

Li, G. & Zhao, X.S., "Characterization and Photocatalytic Propertied of Titanium-Containing Mesoporpus SBA-15", National University of Singapore, Ind. Eng. Chem Res. 2006, vol. 45, pp. 3569-3573.

Liu, Ruili et al., "Triconstitute Co-Assembly to Ordered Mesostructured Polymer-Silica and Carbon-Silica Nanocomposites and Large-Pore Mesoporous Carbons With High Surface Areas", J. Am. Chem. Soc., 2006, vol. 128 (35), pp. 11652-11662.

Fulivio, P. F. et al., "Short-Time Synthesis of SBA-15 Using Various Silica Sources", Kent University, Journal of Colloid & Interface Science vol. 287 (2005) pp. 717-720.

Trukhan, N.N. et al., H2O2-Based Selective Oxidations Over Titaniumsilicates of SBA-15 Type, Microporous and Mesoporous Materials vol. 59 (2003) pp. 73-84, Russia.

(Continued)

*Primary Examiner* — Taylor Victor Oh

(57) ABSTRACT

The present invention relates to an epoxidation process for the preparation of alkylene oxide comprising contacting a hydroperoxide with an olefin in the presence of a catalyst, wherein the catalyst is a titanium containing catalyst obtainable by a method comprising the steps of (a) making a support by a method comprising reacting a silicate with water in the presence of a surfactant selected from block copolymers based on ethylene oxide (EO) and propylene oxide (PO), and calcining the obtained reaction product; and (b) impregnating the support of step (a) with a titanium containing agent.

13 Claims, No Drawings

(56) References Cited

OTHER PUBLICATIONS

Melero, Juan A. et al., Direct Synthesis of Titaniuum-Substituted Mesostructured Materials Using Non-Ionic Surfactants and Titanocene Dichloride, Microporous and Mesoporous Materials, vol. 86 (2005) pp. 364-373.

Zhao, S. et al., "Triblock Copolymer Syntheses of Mesoporous Silica With Periodic 50 to 300 Angstrom Pores", Netherland, Science, 1998, vol. 279. Nr. 5350, pp. 548-552.

Wan, Y. et al, "Designed Synthesis of Mesoporous Solids via Nonionic-Surfactant-Templating Approach", Chem. Commun., 2007, pp. 897-926.

* cited by examiner

EPOXIDATION PROCESS

PRIORITY CLAIM

The present application claims priority from PCT/EP2011/062040, filed 14 Jul. 2011, which claims priority from European application 10170027.6, filed 19 Jul. 2010, which is incorporated herein by reference.

The present invention relates to an epoxidation process for the preparation of alkylene oxide comprising contacting a hydroperoxide with an olefin in the presence of a catalyst.

Titanium catalysts are known to be useful in the preparation of olefin oxide from olefin using a hydroperoxide. Processes for the preparation of titanium catalysts are known. For example, EP 0345856 A discloses a process for making a catalyst suitable for epoxidising olefins using a hydroperoxide, wherein a solid silica is impregnated with a titanium containing agent. In the Example of EP 0345856 A, dried solid silica was used as catalyst support.

CN 101091921 A describes a method of preparing an acrylic epoxidation catalyst, comprising the steps of: a) taking solid silicon oxide and silica sol, add a pore-creating agent and water, shaping, drying and roasting to give silicon oxide carriers, wherein silicon oxide is in a ratio of 1-9 by weight in solid silicon oxide and silica sol; b) putting silicon oxide carrier from step a) into at least one organic solvent selected from methylbenzene, ethylbenzene, hexane, heptane or in cumene, adding titanium source and organic amine, wherein solvent and silicon oxide carrier are in a ratio of 1-10 by weight, the composition mol ratio of reaction mixture is $SiO_2/TiO_2$=10-100, $TiO_2$/Organic amine=0.3-2, to give a titanium-containing molecular sieve; c) filtering, washing and roasting the titanium-containing molecular sieve to give catalyst precursor; d) placing the catalyst precursor under a nitrogen atmosphere and adding at least one organosilicon compound selected from hexa methyl chloride silazane, hepta methyl chloride silazane, trimethylchlorosilane, dimethylchlorosilane, di silazane of tetramethyl, diethoxydimethylsilane, trimethyl methoxy silane, dimethoxy silane or trimethyl ethoxy silane of dimethyl, wherein the organosilicon compound and catalyst precursor are in a ratio of 0.01-0.2 by weight, to give the acrylic epoxidation catalyst.

WO 2004/050233 A describes a process for the preparation of an epoxidation catalyst, which process comprises impregnating a silicon containing carrier with a gas stream consisting of titanium halide. Any silicon containing carrier may be used in the process of WO 2004/050233 A.

The object of the present invention is to find an alternative silicon containing support to be used for preparing a titanium containing catalyst, wherein the latter may be used satisfactorily, in terms of activity and selectivity, in an olefin epoxidation process using a hydroperoxide and such catalyst.

Said object has been achieved in that an alternative silicon containing support as described above was found. More in particular, a support was found which is obtainable by a method comprising reacting a silicate with water in the presence of a surfactant, and calcining the obtained reaction product.

A similar support and a method for making such support are disclosed in Chinese patent application CN 1346791 A. CN 1346791 A does not disclose or suggest the use of said support in the preparation of a titanium catalyst suitable in the preparation of olefin oxide from olefin using a hydroperoxide and said catalyst.

Accordingly, the present invention relates to an epoxidation process for the preparation of alkylene oxide comprising contacting a hydroperoxide with an olefin in the presence of a catalyst, wherein the catalyst is a titanium containing catalyst obtainable by a method comprising the steps of:
(a) making a support by a method comprising reacting a silicate with water in the presence of a surfactant selected from block copolymers based on ethylene oxide (EO) and propylene oxide (PO), and calcining the obtained reaction product; and
(b) impregnating the support of step (a) with a titanium containing agent.

In above-mentioned step (a), a catalyst support is made by a method comprising reacting a silicate with water in the presence of a surfactant selected from block copolymers based on ethylene oxide (EO) and propylene oxide (PO), and then calcining the obtained reaction product.

The silicate to be used in above-mentioned step (a) should react with water. Preferably, said silicate is an orthosilicate of formula $Si(OR)_4$, wherein each R may be the same or different, and may be an alkyl, preferably $C_1$-$C_6$ alkyl, for example methyl, ethyl, propyl or n-butyl. Most preferably, the silicate is tetraethyl orthosilicate of formula $Si(OCH_2CH_3)_4$ (TEOS).

The surfactant that should be present in above-mentioned step (a) is a non-ionic surfactant selected from block copolymers based on ethylene oxide (EO) and propylene oxide (PO). Preferably, said block copolymers based on ethylene oxide (EO) and propylene oxide (PO) have a HLB of from 7 to 12 (HLB=hydrophile-lipophile balance).

Hydrophile-lipophile balance (HLB) is a well-known term in the art which is used, for example, in Zhao et al., Chem. Commun., 2007, 897-926.

Preferably, the surfactant used in the present invention is selected from block copolymers based on ethylene oxide (EO) and propylene oxide (PO) containing 2 hydroxyl groups.

In a preferred embodiment of the present invention, the surfactant is selected from EO/PO-block copolymers having the general formula $HO(CH_2CH_2O)_x(CH_2CH(CH_3)O)_y(CH_2CH_2O)_xH$, wherein x is an integer in the range of from 15 to 150, more preferably in the range of from 15 to 100, even more preferably in the range of from 15 to 50 and most preferably in the range of from 15 to 25 and y is an integer in the range of from 40 to 80.

Difunctional EO/PO-block copolymers, containing 2 hydroxyl groups, that may be advantageously used in the present invention are the polymer series available from BASF under the trade designation "Pluronic". Examples of the latter are "Pluronic P-123" polymer of formula $HO(CH_2CH_2O)_{20}(CH_2CH(CH_3)O)_{70}(CH_2CH_2O)_{20}H$ and "Pluronic P-103" polymer of formula $HO(CH_2CH_2O)_{17}(CH_2CH(CH_3)O)_{56}(CH_2CH_2O)_{17}H$. Most preferably, the surfactant is "Pluronic P-123" polymer.

Upon combining the silicate with water in above-mentioned step (a), a hydrolysis reaction forming silica ($SiO_2$) occurs. Said reaction is exemplified below with reference to TEOS:

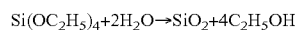
$$Si(OC_2H_5)_4 + 2H_2O \rightarrow SiO_2 + 4C_2H_5OH$$

Said hydrolysis reaction may be catalyzed by a base or an acid. It is preferred that in above-mentioned step (a), the silicate is reacted with water in the presence of an acid catalyst. Such acid may be organic or inorganic. Preferably, the acid is an inorganic acid, for example hydrochloric acid or hydrobromic acid. Most preferably, the acid is hydrochloric acid (HCl).

In above-mentioned step (a), the silicate can be made to react with water by combining the silicate with a mixture comprising water, acid and the surfactant selected from block copolymers based on ethylene oxide (EO) and propylene oxide (PO). Preferably, said surfactant is first dissolved in an acidic aqueous solution before it is combined with the silicate.

The temperature at which said hydrolysis reaction may be carried out, may be of from 10 to 60° C. Preferably, it is higher than ambient temperature, specifically 30 to 60° C., more specifically 35 to 50° C. Further, the hydrolysis reaction may be carried out during a period of time of from 12 to 48 hours, specifically of from 18 to 30 hours.

In the above-mentioned hydrolysis reaction, a silica "gel" is formed. In such process, the orthosilicate molecule is converted into a mineral-like solid via the formation of Si—O—Si linkages. The presence of the surfactant selected from block copolymers based on ethylene oxide (EO) and propylene oxide (PO) during such conversion is thought to be important for the structure of the final silica solid. Said surfactant is a so-called "structure-directing agent".

The side-product of said hydrolysis reaction is an alcohol, such as ethanol when hydrolyzing TEOS. The hydrolysis reaction can be driven to completion by removal of the alcohol from the reaction mixture, for example by (additional) heating. For example, in a case where TEOS is combined with water in the presence of an acid, ethanol may be removed by heating the reaction mixture during a period of time sufficiently long and/or at a temperature sufficiently high to remove substantially all of the ethanol.

An alternative way of driving the above hydrolysis reaction to completion is by adding an alkali metal salt, such as a sodium or potassium salt, preferably a sodium salt. Said alkali metal salt may be an alkali metal halogenide, alkali metal sulphate, alkali metal phosphate, alkali metal hydrogen sulphate, etc., preferably an alkali metal halogenide, even more preferably an alkali metal chloride. Most preferably, said alkali metal salt is sodium chloride (NaCl). The alkali metal salt may be combined with the surfactant before the latter is combined with the silicate, or it may be combined with the silicate before the latter is combined with the surfactant. Further, the alkali metal salt may be added separately.

In the hydrolysis reaction of above-mentioned step (a), the water is in molar excess over the silicate. The weight ratio of the surfactant to the silicate is preferably of from 0.01:1 to 1:1, more preferably 0.1:1 to 0.5:1.

If an acid is used it may be used in a catalytic amount. However, preferably, the acid is in molar excess over the silicate. In case the silicate is combined with a mixture comprising water, acid and the surfactant, the molar concentration of the acid in the latter mixture is preferably of from 0.5 to 2.5, more preferably of from 1 to 2 moles per kg of total mixture.

If an alkali metal salt is used, it may be used in a weight ratio of surfactant to alkali metal salt of from 0.01:1 to 2:1, specifically 0.1:1 to 1:1. The weight ratio of the alkali metal salt to the silicate may vary widely. In general, the greater the weight ratio of the alkali metal salt to the silicate, the lower the hydrolysis reaction temperature can be.

Before the obtained silica material is impregnated with a titanium containing agent in above-mentioned step (b), the surfactant selected from block copolymers based on ethylene oxide (EO) and propylene oxide (PO) should first be removed from the silica material. In above-mentioned step (a), said surfactant is removed by calcining the reaction product that is obtained by reacting the silicate with water. Said reaction product should be calcined during a period of time sufficiently long and at a temperature sufficiently high to effect substantially complete removal of the surfactant. In above-mentioned step (a), the calcining may comprise heating the silica reaction product to a final temperature in the range of from 300 to 900° C., specifically 400 to 800° C., more specifically 500 to 600° C., and then maintaining it at that final temperature during a period of time in the range of from 2 to 15 hours, specifically 3 to 10 hours. Said final temperature may be reached by increasing the temperature at a fixed rate, for example 0.1 to 10° C./min, specifically 0.5 to 5° C./min.

It is preferred that before said calcination in step (a), the reaction mixture that is obtained by reacting the silicate with water is first subjected to hydrothermal heating. The hydrothermal treatment is preferably carried out by heating the reaction mixture at a temperature in the range of from 80 to 120° C., more preferably 90 to 110° C. Said treatment may be carried out during a period of time in the range of from 12 to 48 hours, specifically in the range of from 18 to 30 hours. The solid, hydrothermally treated product so obtained may then be further dried at a temperature in the range of from 30 to 60° C. before it is calcined.

The solid silica obtained in step (a) can be formed into a support for a catalyst by various shaping techniques such a pelletising, extrusion or pressing, crushing and sieving, depending upon the needs of the process in which the catalyst will be used. Alternatively, it can be used as prepared in step (a).

In step (b), the calcined support of step (a) is impregnated with a titanium containing agent.

In a case where in time said calcination is not directly followed by said impregnation, the support of step (a) is preferably first dried at a temperature in the range of from 300 to 800° C., specifically 400 to 700° C., to obtain a dried support to be impregnated in step (b).

The titanium containing impregnating agent to be used in above-mentioned step (b) may be a liquid or gaseous agent. Preferably, it is a gaseous agent.

In a case where the titanium containing impregnating agent is gaseous, above-mentioned step (b) may be performed by contacting the support of above-mentioned step (a) with a gas stream containing titanium halide, for example titanium tetrachloride ($TiCl_4$), to obtain an impregnated support. The temperature during said step (b) may very within wide ranges. Preferably, said temperature is higher than 130° C. and more preferably it is higher than 130° C. and up to 200° C. The pressure during said step (b) may also very within wide ranges.

The amount of gaseous titanium halide supplied in step (b) may be such that the catalyst obtained is loaded with in the range of from 0.1 to 10 wt. % of titanium, based on the total weight of the catalyst. Suitably, said titanium loading is in the range of from 0.5 to 8 wt. %, more suitably in the range of from 1 to 6 wt. %.

Generally, the silica support may be contacted with gaseous titanium halide during a period of time in the range of from 0.1 to 10 hours, more specifically in the range of from 0.5 to 6 hours. Titanium halides which can be used comprise tri- and tetra-substituted titanium complexes which have of from 1 to 4 halide substituents with the remainder of the substituents, if any, being alkoxide or amino groups. The titanium halide can be either a single titanium halide compound or can be a mixture of titanium halide compounds. Preferably, the titanium halide comprises at least 50 wt. % of titanium tetrachloride, more specifically at least 70 wt. % of titanium tetrachloride. Most preferably, the titanium halide is titanium tetrachloride.

Where in step (b) a gas stream comprising titanium halide is used, the gas stream may also comprise an inert carrier gas. If such inert gas is present, the inert gas preferably is nitrogen. A gas stream solely consisting of titanium halide may be used. In the latter case, the preparation is carried out in the absence of a carrier gas. However, limited amounts of other gaseous compounds may be present. The gas in contact with the support during impregnation preferably consists for at least 70 wt. % of titanium halide, more specifically at least 80 wt. %, more specifically at least 90 wt. %, most specifically at least 95 wt. %. Specific preferred processes have been described in EP 1567261A.

Gaseous titanium halide can be prepared in any way known to someone skilled in the art. A simple and easy way comprises heating a vessel containing titanium halide to such temperature that gaseous titanium halide is obtained. If inert gas is to be present, the inert gas can be led over the heated titanium halide.

After step (b), the impregnated catalyst is preferably calcined. Preferably, such calcination is carried out at a temperature of at least 300° C., more preferably at a temperature of at least 400° C., even more preferably at a temperature of at least 550° C. From a practical point of view, the calcination temperature applied is at most 800° C. Preferably, the calcination is carried out at a temperature of at most 650° C. Normally, a calcination time in the range of 30 minutes up to 24 hours is applied.

Generally, a titanium containing catalyst is hydrolysed and optionally silylated before being used in olefin epoxidation. Therefore, after impregnation in step (b) and before use as an olefin epoxidation catalyst, the catalyst is preferably hydrolysed to obtain a hydrolysed catalyst, and the hydrolysed catalyst is then optionally contacted with a silylating agent to obtain a silylated catalyst. Hydrolysis of the catalyst is suitably carried out with steam at a temperature preferably in the range of from 150 to 400° C., more preferably in the range of from 250 to 350° C.

Silylation of the (hydrolysed) catalyst can be carried out by contacting the (hydrolysed) catalyst with a silylating agent, preferably at a temperature of between 100 and 425° C., more preferably at a temperature of between 150 to 350° C. Suitable silylating agents include organosilanes like tetra-substituted silanes with $C_1$-$C_3$ hydrocarbyl substituents. A very suitable silylating agent is hexamethyldisilazane. Examples of suitable silylating methods and silylating agents are, for instance, described in U.S. Pat. Nos. 3,829,392 A and 3,923, 843 A, which are referred to in U.S. Pat. No. 6,011,162 B, and in EP 734764 A.

Further, the present invention relates to the above catalyst preparation method as such, that is to say to a method for preparing a titanium containing catalyst, preferably for use in an epoxidation process comprising contacting a hydroperoxide with an olefin in the presence of a catalyst, wherein the method comprises above-mentioned steps (a) and (b). The above embodiments and preferences regarding said steps (a) and (b) as described with reference to the present epoxidation process also apply to said catalyst preparation method as such.

Still further, the present invention relates to the catalyst which is obtainable by said catalyst preparation method.

In the present invention, the titanium containing catalyst that is obtainable by a method comprising above-mentioned steps (a) and (b) is used in an epoxidation process comprising contacting a hydroperoxide with an olefin in the presence of said catalyst.

In the present epoxidation process, the olefin to be epoxidised may be ethylene or propylene, preferably propylene, resulting in ethylene oxide and propylene oxide, respectively. The hydroperoxide in said epoxidation process may be hydrogen peroxide or an organic hydroperoxide. Preferably, the hydroperoxide is an organic hydroperoxide. The organic hydroperoxide may for example be tert-butyl hydroperoxide (TBHP), cumene hydroperoxide (CHP) or ethylbenzene hydroperoxide (EBHP). Using an organic hydroperoxide results in the co-production of the alcohol corresponding to said hydroperoxide.

Therefore, the present invention further relates to a process for the preparation of alkylene oxide which process comprises contacting an organic hydroperoxide and alkene with a heterogeneous epoxidation catalyst and withdrawing a product stream comprising alkylene oxide and an alcohol, in which process the catalyst is obtainable by a method comprising above-mentioned steps (a) and (b). The above embodiments and preferences regarding said steps (a) and (b) as described with reference to the epoxidation process in general also apply to said specific alkylene oxide preparation process.

A specific organic hydroperoxide that can be used in the present epoxidation process is ethylbenzene hydroperoxide (EBHP), in which case the alcohol obtained is 1-phenylethanol. The 1-phenylethanol may be converted into styrene by dehydration. EBHP is preferably used to make propylene oxide in the present epoxidation process. EBHP can be made by reaction of ethylbenzene with oxygen.

Another process for producing propylene oxide is the co-production of propylene oxide and methyl tert-butyl ether (MTBE). This process is well known in the art and involves similar reaction steps as the above-described styrene/propylene oxide production process. In the epoxidation step tert-butyl hydroperoxide is reacted with propene forming propylene oxide and tert-butanol. Tert-butanol is subsequently etherified into MTBE.

A further process comprises the manufacture of propylene oxide with the help of cumene. In this process, cumene is reacted with oxygen or air to form cumene hydroperoxide. Cumene hydroperoxide thus obtained is reacted with propene in the presence of an epoxidation catalyst to yield propylene oxide and cumyl alcohol. The latter can be converted into cumene with the help of a heterogeneous catalyst and hydrogen. Specific suitable processes are described for example in WO 02/48126 A.

The conditions for the epoxidation process according to the present invention are those conventionally applied. For propene epoxidation with the help of ethylbenzene hydroperoxide, typical reaction conditions include temperatures of 50 to 140° C., suitably 75 to 125° C., and pressures up to 80 bar with the reaction medium being in the liquid phase.

The invention is further illustrated by the following Examples.

EXAMPLES

Example 1

In a first step (a), the support material for the catalyst was prepared. In a 100 l autoclave, 0.5 kg of surfactant "Pluronic P-123" polymer ex. BASF and 1.0 kg of sodium chloride (NaCl) were added over a period of 4.5 hours, while stirring, to a solution comprising 5 kg of a 35.5 wt. % hydrochloric acid (HCl) aqueous solution and 30 kg of water. The molar HCl concentration of the obtained mixture was 1.3 moles per kg of total mixture.

After the surfactant was completely dissolved, 2.08 kg of tetraethyl orthosilicate (TEOS) was added to the obtained solution. The solution was stirred at 40° C. for 20 hours thereby forming a gel containing mixture. This reaction mixture was subjected to hydrothermal treatment at 100° C. for 24 hours in the autoclave. After centrifuging and further drying at 40° C., a white powder was obtained. This powder was calcined by heating to 550° C. at a fixed rate of 0.5° C./min and heating at 550° C. for 6 hours to remove the surfactant.

The resulting silica powder was pressed in a hydraulic press for 3 minutes at 2000 kg/cm². The resulting solid was crushed manually and sieved to a support material with a particle size distribution of 0.6-1.8 mm.

In a second step (b), the support material so obtained was impregnated with a titanium containing agent.

The support material so obtained was contacted with a gas stream consisting of titanium tetrachloride. The gas stream was obtained by heating titanium tetrachloride to 200° C. with the help of an electrical heating system. The support material was contacted with such amount of gaseous titanium tetrachloride that the catalysts obtained were loaded with 4.03 wt. % of titanium, respectively, based on the total weight of the catalyst.

The impregnated catalyst thus obtained was calcined at 600° C. during 7 hours. The calcined catalyst was subsequently contacted with steam at 325° C. during 6 hours. The steam flow consisted of 3 grams of water per hour and 8 Nl of nitrogen per hour. Finally, the catalyst was silylated at 185° C. during 2 hours by being contacted with 18 grams of hexamethyldisilazane per hour in a nitrogen flow of 1.4 Nl per hour.

Example 2 (Comparative)

The silica gel carrier used in this Example was that obtainable from Grace under the trade designation "P543". Said silica gel had a surface area of 300 m²/g and a weight average particle size of about 1 mm. Substantially all particles had a particle size between 0.6 and 1.4 mm.

75 grams of this silica gel carrier was dried at different temperatures during 2 hours.

Subsequently, the dried silica gel carrier thus obtained was contacted with a gas stream consisting of titanium tetrachloride. The gas stream was obtained by heating titanium tetrachloride to 200° C. with the help of an electrical heating system.

The silica carrier was impregnated such as to obtain an impregnated carrier containing 3.75 wt. % of titanium on total amount of impregnated carrier.

The impregnated catalyst thus obtained was calcined at 600° C. during 7 hours. The calcined catalyst was subsequently contacted with steam at 325° C. during 6 hours. The steam flow consisted of 3 grams of water per hour and 8 Nl of nitrogen per hour. Finally, the catalyst was silylated at 185° C. during 2 hours by being contacted with 18 grams of hexamethyldisilazane per hour in a nitrogen flow of 1.4 Nl per hour.

Catalyst Epoxidation Screening Test

The catalyst and the comparative catalyst of Examples 1 and 2 were tested in parallel reactors under identical conditions (temperature, pressure and feed composition).

Test Conditions:

0.4 g catalyst with a typical particle size of 0.18-0.30 mm was loaded in a 40 cm×1.76 mm ID RVS reactor tube. All reactor tubes were mounted in the same oil circulation bath and were operated at the same isothermal conditions.

Ethylbenzene hydroperoxide (EBHP) as a 36% w/w solution in ethyl benzene and propylene were pressurized and mixed in a mole ratio of 6 (mol/mol propylene/EBHP).

This reaction mixture was fed to the liquid full reactors at a typical WHSV of 16 g/gh at a pressure of 40 bar. The temperature was maintained at 60° C. for the first 7 days and then elevated to 62° C. over the course of 2.5 days.

The feed and the product composition after epoxidation were analyzed by GC with a high-pressure injector.

Parameters of activity, selectivity and deactivation as function of time were calculated and compared with batches of comparative catalyst tested by the same method.

The following results for activity were obtained:

TABLE

| Activity (g of PO/g catalyst/hour | 0 hour | 75 hours | 150 hours | 225 hours |
|---|---|---|---|---|
| Working Catalyst | 1.20 | 1.07 | 1.08 | 1.04 |
| Comparative Catalyst | 1.20 | 1.02 | 0.97 | 0.92 |

As is clearly visible from the above results, the deactivation of the working catalyst over time is considerably less than for the comparative catalyst, which will lead to much longer times on stream and/or higher selectivities due to lower operating temperatures.

What is claimed is:

1. An epoxidation process for the preparation of alkylene oxide comprising contacting a hydroperoxide with an olefin in the presence of a catalyst, wherein the catalyst is a titanium containing catalyst obtainable by a method comprising the steps of:
   (a) making a support by a method comprising reacting a silicate with water in the presence of a surfactant selected from block copolymers based on ethylene oxide (EO) and propylene oxide (PO), and calcining the obtained reaction product;
   (b) impregnating the support of step (a) with a titanium containing agent to obtain an impregnated catalyst;
   (c) calcining the impregnated catalyst of step (b);
   (d) hydrolyzing the calcined impregnated catalyst of step (c) with steam at a temperature in the range of from 150 to 400° C; and
   (e) silylating the hydrolyzed impregnated catalyst of step (d) with a silylating agent.

2. A process according to claim 1, wherein the silicate in step (a) is an orthosilicate of formula $Si(OR)_4$, wherein each R is the same or different, and is an alkyl.

3. A process according to claim 1, wherein the surfactant is selected from block copolymers based on ethylene oxide (EO) and propylene oxide (PO) containing 2 hydroxyl groups.

4. A Process according to claim 1, wherein the surfactant is selected from EO/PO-block copolymers having the formula $HO(CH_2CH_2O)_x(CH_2CH(CH_3)O)_y(CH_2CH_2O)_xH$, wherein x is an integer in the range of from 15 to 150 and y is an integer in the range of from 40 to 80.

5. A process according to claim 1, wherein the surfactant have the chemical formula selected from the group consisting of $HO(CH_2CH_2O)_{20}(CH_2CH(CH_3)O)_{70}(CH_2CH_2O)_{20}H$ and $HO(CH_2CH_2O)_{17}(CH_2CH(CH_3)O)_{56}(CH_2CH_2O)_{17}H$.

6. A process according to claim 1, wherein the calcining in step (a) comprises heating the reaction product to a final temperature of from 300 to 900° C. and then maintaining it at that final temperature during a period of time of from 2 to 15 hours.

7. A process according to any claim 1, wherein the titanium containing agent in step (b) is a gaseous agent.

8. A process according to claim 1, wherein the hydroperoxide is an organic hydroperoxide and wherein a product stream comprising alkylene oxide and an alcohol is withdrawn.

9. A process according to claim 8, wherein the organic hydroperoxide is tert-butyl hydroperoxide, cumene hydroperoxide or ethylbenzene hydroperoxide.

10. A process according to claim 9, wherein the organic hydroperoxide is ethylbenzene hydroperoxide and the alcohol is 1-phenylethanol, further comprising the step of dehydration of 1-phenylethanol into styrene.

11. A process according to claim 1, wherein the impregnated catalyst of step (b) is calcined in step (c) at a temperature of at least 300° C.

12. A process according to claim 1, wherein the silylating agent is a tetra-substituted silane with C1 to C3 hydrocarbyl substitutes.

13. A process according to claim 1, wherein the hydrolyzed impregnated catalyst of step (d) is silylated with a silylating agent at a temperature of between 100 to 425° C.

* * * * *